(12) United States Patent
Al Shammari

(10) Patent No.: US 11,730,495 B2
(45) Date of Patent: Aug. 22, 2023

(54) METHOD FOR TREATING A SUPRACONDYLAR FRACTURE

(71) Applicant: Imam Abdulrahman Bin Faisal University, Dammam (SA)

(72) Inventor: Sulaiman Mohammed Al Shammari, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 52 days.

(21) Appl. No.: 17/549,111

(22) Filed: Dec. 13, 2021

(65) Prior Publication Data

US 2022/0096102 A1    Mar. 31, 2022

Related U.S. Application Data

(62) Division of application No. 16/447,292, filed on Jun. 20, 2019, now Pat. No. 11,224,446.

(51) Int. Cl.
*A61B 17/17* (2006.01)
*A61B 17/88* (2006.01)
*A61B 17/72* (2006.01)
*A61B 17/90* (2006.01)

(52) U.S. Cl.
CPC ...... *A61B 17/1739* (2013.01); *A61B 17/8897* (2013.01); *A61B 17/1725* (2013.01); *A61B 17/72* (2013.01); *A61B 17/90* (2021.08)

(58) Field of Classification Search
CPC ...................... A61B 17/17–1796; A61B 1/317
See application file for complete search history.

(56) References Cited

U.S. PATENT DOCUMENTS

| | | | |
|---|---|---|---|
| 5,030,219 | A | 7/1991 | Matsen, III |
| 5,769,856 | A | 6/1998 | Dong |
| 5,836,950 | A | 11/1998 | Hansson |
| 10,405,993 | B2 | 9/2019 | Deransart |
| 2008/0021479 | A1 | 1/2008 | Penenberg |
| 2009/0112208 | A1 | 4/2009 | Borgia |
| 2014/0214045 | A1 | 7/2014 | Felder et al. |
| 2015/0066041 | A1 | 3/2015 | Kim |
| 2016/0074049 | A1 | 3/2016 | Russell |
| 2018/0110530 | A1 | 4/2018 | Wagner |
| 2018/0289379 | A1 | 10/2018 | Dacosta et al. |
| 2019/0350576 | A1 | 11/2019 | Ingwer |
| 2021/0204967 | A1 | 7/2021 | Lefebvre |

FOREIGN PATENT DOCUMENTS

| | | |
|---|---|---|
| CN | 205964148 U | 2/2017 |
| CN | 108030541 A | 5/2018 |
| DE | 100 39 690 A1 | 2/2002 |

*Primary Examiner* — Matthew J Lawson
(74) *Attorney, Agent, or Firm* — Oblon, McClelland, Maier & Neustadt, L.L.P.

(57) ABSTRACT

The invention is directed to a surgical device which is externally used as aiming device that permits accurate placement of surgical wire to mend a supracondylar fracture. The device of the invention decreases operative time, risks of the re-dislocation through continuous manipulation, radiology exposure for both the patient and operation room staff, and to decreases anesthesia duration. It is also directed to surgical use of the device for repair of a supracondylar fracture and to methods for making it.

16 Claims, 9 Drawing Sheets

FIG. 5A
FIG. 5B
FIG. 5C
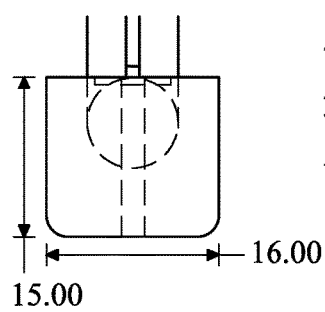
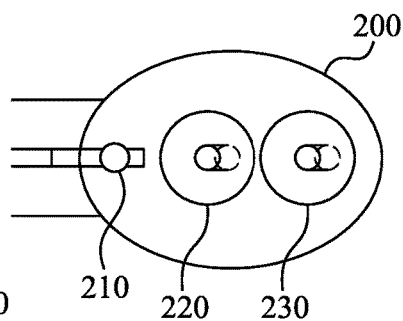
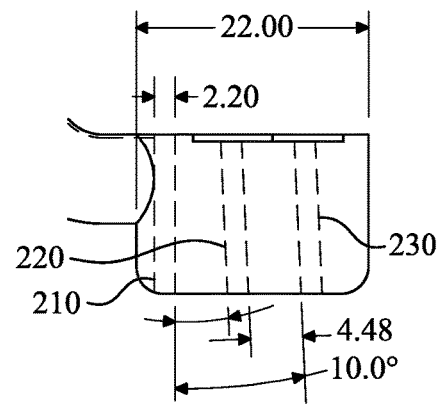
FIG. 5D
FIG. 5E
FIG. 5F
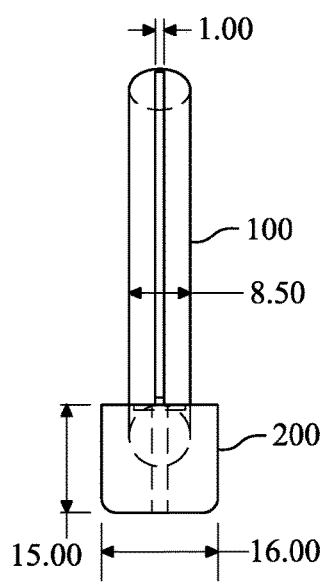
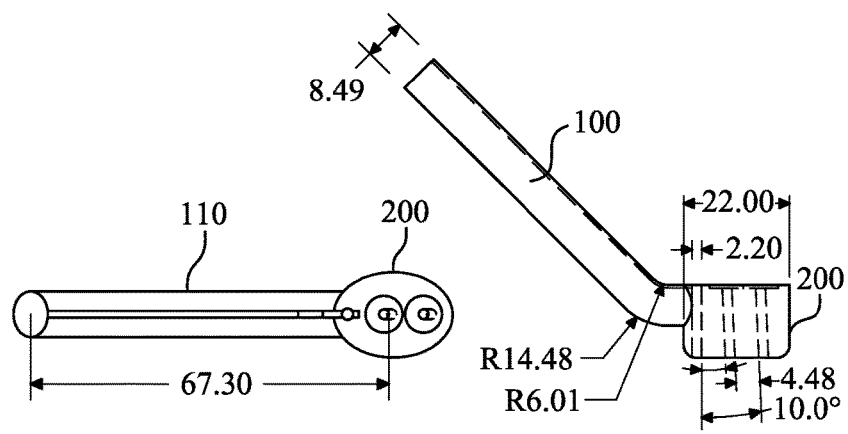

METHOD FOR TREATING A SUPRACONDYLAR FRACTURE

CROSS-REFERENCE TO RELATED APPLICATIONS

The present application is a Divisional of U.S. application Ser. No. 16/447,292, now allowed, having a filing date of Jun. 20, 2019.

BACKGROUND OF THE INVENTION

Field of the Invention

The invention pertains to the field of medicine, more specifically to surgery and to a device and method to assist and guide wire fixation in pediatric humeral supracondylar fractures.

Description of Related Art

A supracondylar humerus fracture is a fracture of the distal humerus just above the elbow joint. The fracture is usually transverse or oblique and above the medial and lateral condyles and epicondyles. This fracture pattern is relatively rare in adults, but is the most common type of elbow fracture in children. In children, many of these fractures are non-displaced and can be treated with casting. Some are angulated or displaced and are best treated with surgery. In children, most of these fractures can be treated effectively with expectation for full recovery. Some of these injuries can be complicated by poor healing or by associated blood vessel or nerve injuries with serious complications.

Swelling and vascular injury following the fracture can lead to the development of compartment syndrome which leads to long-term complication of Volkmann's contracture (fixed flexion of the elbow, pronation of the forearm, flexion at the wrist, and joint extension of the metacarpophalangeal joint). Therefore, early surgical reduction is indicated to prevent this type of complication. The distal humerus grows slowly post fracture (only contributes 10 to 20% of the longitudinal growth of the humerus); therefore, there is a high rate of malunion if the supracondylar fracture is not corrected appropriately. Such malunion can result in cubitus varus deformity. This in turns results in tardy ulnar nerve palsy due to the stretching of the ulnar nerve behind the medial epicondyle of the humerus.

Vascular insufficiency as characterized by the absence of the radial pulse is reported in 6 to 20 percent of all supracondylar fractures. Vascular injury evident by involvement of brachial artery is most commonly associated with Type II and III supracondylar fractures, frequently encountered in postero-laterally displaced fractures. Patients without significant improvement in pulse after orthopedic care, warrant emergent vascular exploration, especially if there is intractable pain, persistence of pain or increasing pain despite of fracture site stabilization which is suggestive of ischemia.

The frequency of neurologic deficit reported after supracondylar fractures in children is 10 to 20 percent and increases in some series of children with Type III supracondylar fractures to as high as 49 percent. Median nerve and its anterior interosseous nerve branch is at risk and gets most commonly involved in postero-lateral displacement of the distal fracture fragment, whereas radial nerve is most commonly involved with postero-medial displacement of the distal fracture fragment. Ulnar nerve injuries are commonly associated with flexion type supracondylar fracture.

Forearm compartment syndrome resulting in Volkmann's Ischemic Contracture: Vascular injury and primary swelling from the injury can lead to the development of compartment syndrome within 12 to 24 hours. If a compartment syndrome is not treated timely, the associated ischemia may progress to infarction and subsequent development of Volkmann's ischemic contracture: fixed flexion of the elbow, pronation of the forearm, flexion at the wrist, and joint extension of the metacarpal-phalangeal joint.

One of the frequent long term complications of supracondylar fracture is an angular deformity, of which cubitus varus or "gunstock" deformity is very common. The distal humerus physis, in contrast to the proximal humeral physis, contributes only 15 to 20 percent to the overall longitudinal growth of the humerus. This suggests very limited remodeling in correction of fracture angulation in children with supracondylar fractures Guidelines for treatment of pediatric supracondylar humerus fractures have been established; see The Journal of the American Academy of Orthopaedic Surgeons 20(5):328-30. May 2012, *AAOS Clinical Practice Guideline: The Treatment of Pediatric Supracondylar Humerus Fractures* DOI: 10.5435/JAAOS-20-05-328 which is incorporated by reference.

Currently, there are no systems available to assist in the process of wire fixation for pediatric supracondylar fractures. Instead, the surgeon must depend on visual assessment and freehand placement of wires during the procedure. This increases the time, cost and risk of the surgery and often results in significant variation of surgical outcomes.

In view of the problems with existing surgical procedures, the inventor sought to provide a guide to shorten surgical time and to provide for more exact and uniform surgical results in pediatric patients having supracondylar fractures.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

In one aspect the surgical device of the present disclosure is an externally placed aiming device that permits accurate insertion and placement of surgical wire or surgical reinforcement to mend a supracondylar fracture. This surgical device can decrease operative time, decrease risks of re-dislocation through continuous manipulation, radiology exposure for both the patient and operation room staff, and decrease duration of anesthesia. The device provides a fixed angle guide and guide for distance between fixating wires and/or other reinforcement, thus producing optimum radiographic and clinical results. The surgical device makes the repair of the fracture, especially in young children, safer, simpler, and more economical.

Various non-limiting embodiments of the invention are described by the following paragraphs.

In one embodiment, the present disclosure is directed to a surgical device that includes a handle suitable for a surgeon to move, steer or otherwise position the device on skin, such as skin over or around the humerus, where the handle has a longitudinal groove aligned with holes A, B and C suitable for visual alignment of surgical wires introduced into the device (such as a groove that is about <0.1, 0.1, 0.2, 0.3, 0.4, 0.5, or >0.5 wide and/or deep), and a functional unit which is suitable to hold and guide surgical wire, wherein the handle is about 50, 55, 60, 65, 70, 75, 80, 85, 90, 95 to 100 mm long and has an average width of about 5, 6, 7, 8, 9-10 mm; and wherein the functional unit has an anterior and a posterior side which may be a regular or irregular cylindrical shape and has an average cross-sectional diameter ranging from about 15, 20, 25 to about 30 mm, a vertical thickness ranging from about 10, 11, 12, 13, 14, 15, 16, 17, 18, 19 to about 20 mm, and wherein the functional unit comprises holes A, B and optionally, C, each about 1.7, 1.8, 1.9, 2.0 to 2.1 mm in diameter said holes penetrating the anterior and posterior surfaces of the functional unit and are typically linearly aligned with each other wherein holes A and B, and holes B and C, when C is present, are about 4, 4.5, 5.0, 5.5, to about 6 mm fixed distance from one another, wherein the holes A, B and C vertically penetrate the top and bottom surfaces of the functional unit, wherein a vertical alignment of holes A and B, and holes A and C diverge by about 3, 4, 5, 6, 7, 8, 9, 10, 11, 12, 13, 14, 15, 16, 17, 18, 19 to about 20 degrees, and wherein an inset located around hole B, and hole C, when present, includes a radio-opaque washer-like metal marker. wherein the handle is angled or curved at its lower end to one side along the height of the functional unit at an angle ranging from about 30, 35, 40, 45, 40, 55 to about 60 degrees, and holes A, B and C are linearly aligned with the groove along the longitudinal axis of the handle and the groove reaches hole A, wherein the axis of a anterior cylindrical surface of the functional unit forms a 30-60 degree angle, preferably about 40-50 degrees and most preferably about 45 degree angle, with the longitudinal axis of the handle.

In another embodiment the surgical device as disclosed herein includes a handle that has a substantially circular, elliptical, or oval cross-section, wherein the handle is connected at its lower end to one side along the height of the functional unit at an angle ranging from about 40, 41, 42, 43, 44, 45, 46, 47, 48, 49 to about 50 degrees. The functional unit has a substantially circular or oval or elliptical cross-section which comprises holes A, B and C which have substantially round or oval cross-sections and may have a surrounding depression or inset to accommodate radio-opaque markers. An elliptical cross-section may be measured across its major or minor axis and an oval cross-section may be measured along its longest axis to determine a minimum or maximum diameter.

In preferred embodiments the anterior surface of the functional unit, which faces the skin when in use has a smooth and/or rounded surface so that it can be easily glided or moved over the skin.

In another embodiment, the surgical device as disclosed herein has a substantially circular, elliptical, or oval cross-section and is about 54, 55, 60, 65, 70 to about 74 mm long, the functional unit has a substantially circular, elliptical, or oval cross section having an average diameter of about 20, 21, 22, 23 to about 24 mm, a vertical thickness ranging from about 13, 14, 15, 16 to about 17 mm that comprises holes A, B and C.

In some embodiments, holes A, B and/or C have substantially round, elliptical, or oval cross sections about 1.8-2.0 in diameter, a vertical alignment holes A and B and holes A and C that diverges by about 3, 4, 5, 6, 7, 8, 9, 10, 11, 12, 13, 14, 15, 16, 17, 18, 19 to about 20 degrees and holes A and B, and holes B and C are about 4-6 mm fixed distance from one another.

In other embodiments, the surgical device as disclosed herein may have the handle with a substantially circular, elliptical, or oval cross-section and about 64 mm long and the handle is connected at its lower end to one side along the height of the functional unit at an angle of about 45 degrees. In some embodiments a ratio of the length of the handle to its width, thickness, or diameter ranges from about 20:1, 15:1, 10:1 to 5:1 or any intermediate ratio within this range.

The functional unit may have a substantially circular, elliptical, or oval cross section having an average diameter of about 22 mm, a vertical thickness of about 15 mm, and can comprise holes A, B and C said holes comprising substantially round, elliptical, or oval cross sections about 1.7, 1.9 or 2.1 mm in diameter. In this embodiment the vertical alignment of holes A and B and holes A and C diverges by about 3 to 20 degrees and holes A and B, and holes B and C are about 5 mm fixed distance from one another.

Holes A and B or A, B and C may be spaced apart at distances that provide sufficient divergence between a first introduced wire and a second fixed wire to obtain an excellent resilient fixation. Representative spacings include <4, 4, 4.25, 4.5, 4.75, 5, 5.25, 5.5, 5.75, 6.0 and >6.0, most preferably about 5 mm.

In some embodiments of the device disclosed herein holes B and C are present and the vertical alignment holes A and B and holes A and C is at the same angle between 3 and 20 degrees. In other embodiments, both holes B and C are present and the vertical alignment holes A and B and holes A and C is at different angles between 3 and 30 degrees.

Another embodiment of the invention is directed to a method for treating a supracondylar fracture including reducing the fracture, steering, locating or moving the device as disclosed herein to a location on the skin of a subject proximal to the fracture, introducing K-wire or other surgical wire, screws or fixtures, through into hole B and, optionally, into hole C, and into one or more bones or bone fragments of the subject. In preferred embodiments, all wires are inserted into the body via holes A, B and C in a specified order after a surgeon finds the correct insertion position In some embodiments of the method of treatment using the device disclosed herein, a subject will have a Type I, Type IIA or Type II, Type IIIA or Type IIIB, or Type IV supracondylar fracture. In some types of fractures, such as Type 1 fractures, no or little reduction of the fracture is required before treatment with surgical wire positioned using the device. In other subjects a closed or open, typically closed, reduction of the fracture is performed, typically before, treatment using the device.

In some embodiments of this method of treatment, the subject is less than 1, 2, 3, 4 or 5 years old. In other embodiments, the subject is >5, 6, 7, 8, and no more than 9 years old. In still other embodiments, the subject is 9, 10, 11, 12, 13, 14, 15, 16, 17, 18, 19, 20, 21 or >21 years old. In other embodiments, the subject may be at least 25, 30, 35, 40, 45, 50, 55, 60, 65, 70, 75, 80, 85, 90, 95, 100 or >100 years old.

In some embodiments of this method of using the device disclosed herein a subject has or is at risk of vascular insufficiency due to the supracondylar fracture; has or is at risk of neurological deficit due to the supracondylar fracture; has or is at risk of forearm compartment syndrome associated with the supracondylar fracture; has or is at risk of malunion associated with the supracondylar fracture.

Another embodiment of the invention is directed to a kit comprising at least one of the surgical devices as disclose herein, surgical wire such as K-wire which may have different gauges, packing materials, and instructions for use for treatment of a supracondylar fracture. Preferably, the device is customized to the fracture to be treated.

Another kit may or may not have all these elements and may or not be customized, but may contain two or more of the surgical devices as disclosed herein, for example, where holes A and B, or A and C, have different degrees of vertical divergence, for example, wherein the vertical alignment holes A and B and holes A and C of each surgical device are aligned at different angles between 3 and 20 degrees such as at angles of 3, 4, 5, 6, 7, 8, 9, 10, 11, 12, 13, 14, 15, 16, 17, 18, 19, or 20 degrees from each other, where spacing between holes A and B or A and C varies from device to device, or wherein the holes A, B and C have different sizes that accommodate surgical wires having different diameters.

Another embodiment of the invention is directed to a method for making the surgical device disclosed herein. This method may include conventional construction and machining of the device or may employ 3D printing techniques.

Drilling, puncturing, casting or printing (voids) to form holes A, B and/or C may be used to produce the device with holes A, B and/or C.

During or after production of holes A, B and/or C a radio-opaque marker may be placed in or around the holes, for example, the holes may be produced with an inset or depression of the posterior surface of the device around holes B and C and then equipped with radio-opaque washer-like metal markers or other radio-opaque markers. When 3D printing does not produce an end producing containing these holes, they may be drilled or otherwise produced in the unfinished 3D printed device.

In some embodiments, the method of making the device further includes imaging a supracondylar fracture thereby producing imaging data describing the supracondylar fracture, designing the surgical device including selecting the size of the handle and functional unit and the vertical alignment of holes A, B, and C, when present, from the imaging data thereby custom designing the surgical device, and 3D printing the custom-designed surgical device, and, incorporating comprises a radio-opaque washer-like metal marker in or around holes B and/or C.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIGS. 4A and 4B show x-rays of supracondylar fracture. FIGS. 4C and 4D show radiographic images of insertion of surgical wires into fractured bone. FIGS. 4E and 4F show radiographic images of insertion of surgical wire using bullet sleeve according to the invention. Radio-opaque washer-like elements in holes B and C are visible in lower portion of FIG. 4E which shows alignment of bullet sleeve with humerus and insertion of surgical wire into humerus. A humerus bone (R, right) with a supracondylar fracture is shown by operating room X-ray image. FIGS. 4C and 4D depict the AP-view and FIGS. 4E and 4F depict a side view. The bullet sleeve is circled in the lower part of FIG. 4E. With help of the bullet sleeve the wires can be bent in as a final step while the bullet sleeve holds the wires in place and prevents any displacement or movement of the wires s as shown by FIG. 4E. As visually apparent from these figures, the wires are central and parallel and are easily and safely bent by the bullet sleeve thus making fixation easier, more accurate and meticulous. In FIGS. 4A-4F the Kirschner wire itself is used to fix the fracture.

FIGS. 5A-5F show design details of a 3 holed bullet sleeve as disclosed herein.

FIGS. 5B and 6C show the positions for placement of metal, washer-like elements that can be seen under X-ray and which help positioning wires inserted using the device.

DETAILED DESCRIPTION OF THE INVENTION

Figure 1:
FIG. 1. Intraoperative X-Ray of a humerus fixated by four Kirschner wires (prior art). This file is licensed under the Creative Commons Attribution-Share Alike 3.0 Unported license. Author: Júlio Reis.

The medical device disclosed herein is also known as a supracondylar bullet sleeve because the device enables rapid reduction and stabilization of a supracondylar fracture at the metaphorical speed of a bullet. This device was developed primarily to assist and guide wire, support and/or reinforcement fixation in pediatric humeral supracondylar fractures.

Currently, there are no systems available to assist in the process of wire fixation for a pediatric supracondylar fracture. Thus, wire fixation in a pediatric fracture depends on the skill and experience of the surgeon and depends on visual assessment and on the surgeon's free hand. This often results in significant variations in desired outcomes.

The supracondylar bullet sleeve of the present disclosure is a precise aiming and steering device. Its use decreases fracture fixation time and surgical risks. These risks include those associated re-dislocation due to prolonged or continuous manipulation, radiological exposure of the patient and operating room staff during a radiologically guided surgery, and risks to the patient associated with prolonged anesthesia. Other risks include pin tract infection, breakage of a surgical wire, loss of fixation of a surgical wire, and migration of a surgical wire. The device as disclosed herein reduces these risks by making fixation of a supracondylar fracture faster and more precise.

The device as disclosed herein can provide textbook recommended outcomes if an operator follows simple operation instructions. The device, which adheres to internationally accepted principles for fixation, produces optimal sought-after outcomes by providing a guide providing predetermined fixed divergence angles between the surgical wire holes (e.g., holes for Kirschner wires) along with a recommended distance between them, producing optimum radiographic and clinical results. This device can be customized to a particular fracture, for example, by selection of the divergence angles of, and distance between, surgical wires based on radiological data about the fracture and 3D printing of the supracondylar bullet sleeve.

A design for the device disclosed herein may consider one or more, preferably all, of the following parameters: (i) selection of two or three parallel lateral entry holes (e.g., holes A and B, or holes A, B and C); (ii) selection of a minimum distance between these holes (e.g., about 5 mm between each pin or surgical wire tract provided by holes A and B or holes A, B and C; (iii) selection of a designated divergence angle between each pin tract provided by holes A and B, or holes A, B and C, ranging from about 3 degrees to about 20 degrees; and (iv) selection of four cortices of the entry pin or surgical wire. Holes A, B and C are typically selected to provide a tight fit for the surgical wires or pins used in fixing the supracondylar fracture, for example, their inside diameters may independently from one another range in size from <0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, to >2.5 mm.

In typical embodiments, the supracondylar bullet sleeve of the invention incorporates a functional unit which is configured to hold and guide the fixating wires and/or other orthopedic support or repair pins for stabilization of fractured bones. After surgical reduction of the fracture, a first K-wire is typically introduced in a free hand manner following the principle of fixation after an adequate reduction.

Figure 2:
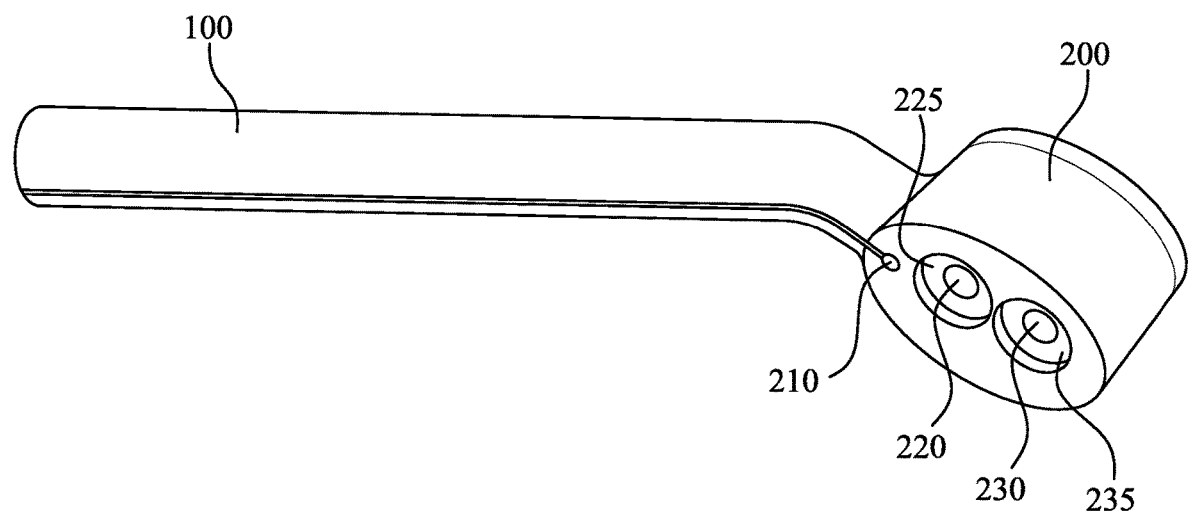
FIG. 2. Photo of a three-holed embodiment of the bullet sleeve: handle (100), functional unit (200). Hole A (210), hole B (220), hole C (230). Radio-opaque washer-like material around hole B (225) and around hole C (235).

The functional unit can be of any suitable shape, but typically has an oval or elliptical or round design containing holes A and B or holes A, B and C as shown by reference characters 210, 220 and 230 in FIG. 2. The third hole C is optional and can be used for procedures where the subject is an older child whose fracture may require three instead of two lateral screws or wires.

Figure 3A:
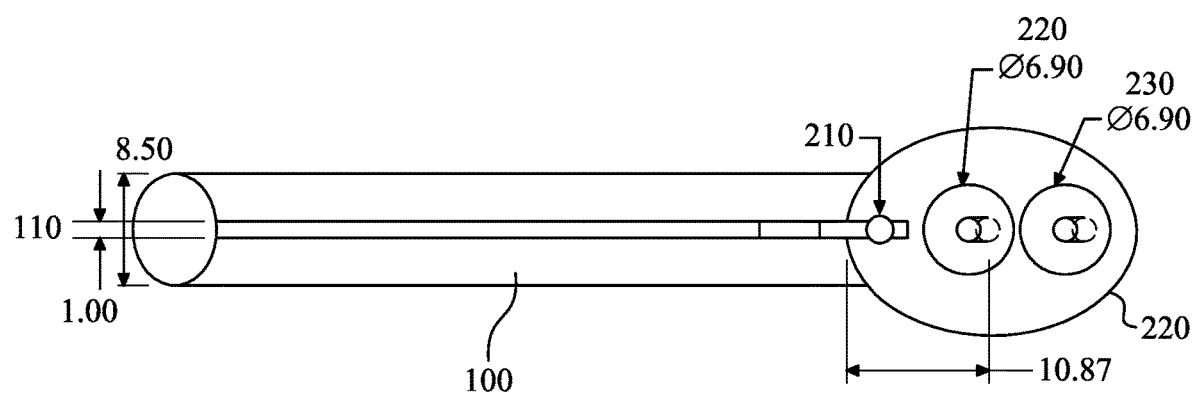
FIG. 3A. Design details of one embodiment of a 3 holed bullet sleeve (230) (top view). Handle (100), (groove in handle (110), functional unit (200) containing hole A (210), hole B (220), and hole C (230).
Figure 3B:
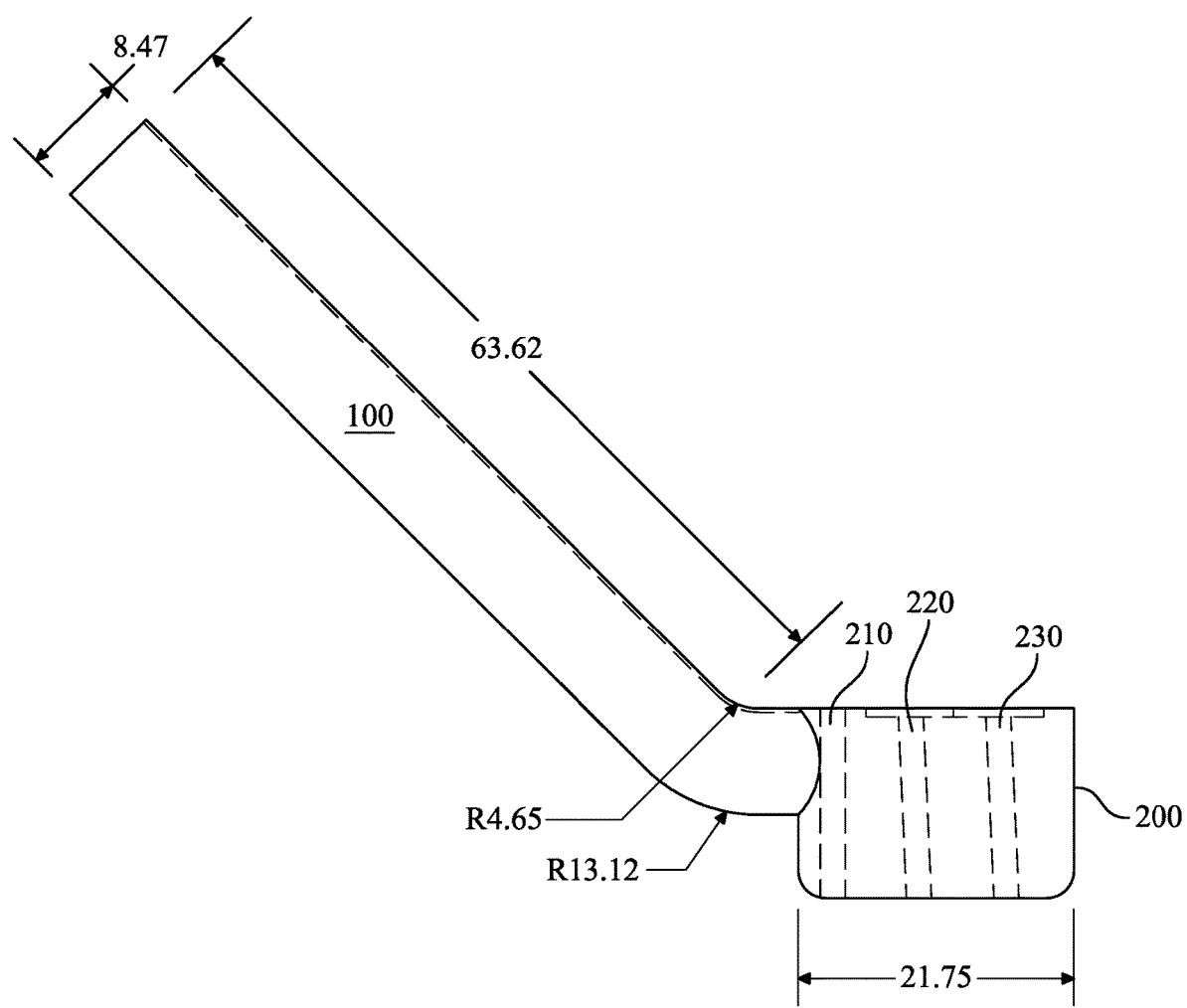
FIG. 3B. Design details of one embodiment of the bullet sleeve (side view). Handle (100), functional unit (200), hole A (210), hole B (220) and hole C (230). The angles of holes B and C as shown are about 3 to 20 degrees divergent to that of hole A.
Figure 3C:
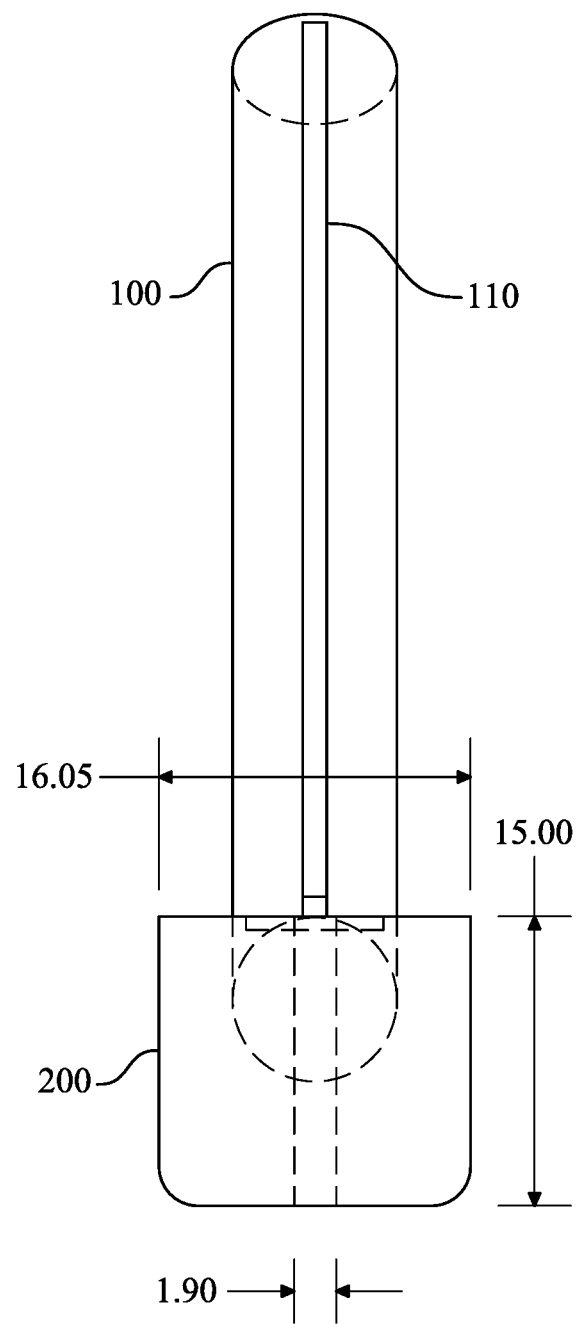
FIG. 3C. Design details of one embodiment of the bullet sleeve (longitudinal view). Handle (100), groove in handle (110), and functional unit (200).
Figure 3D:
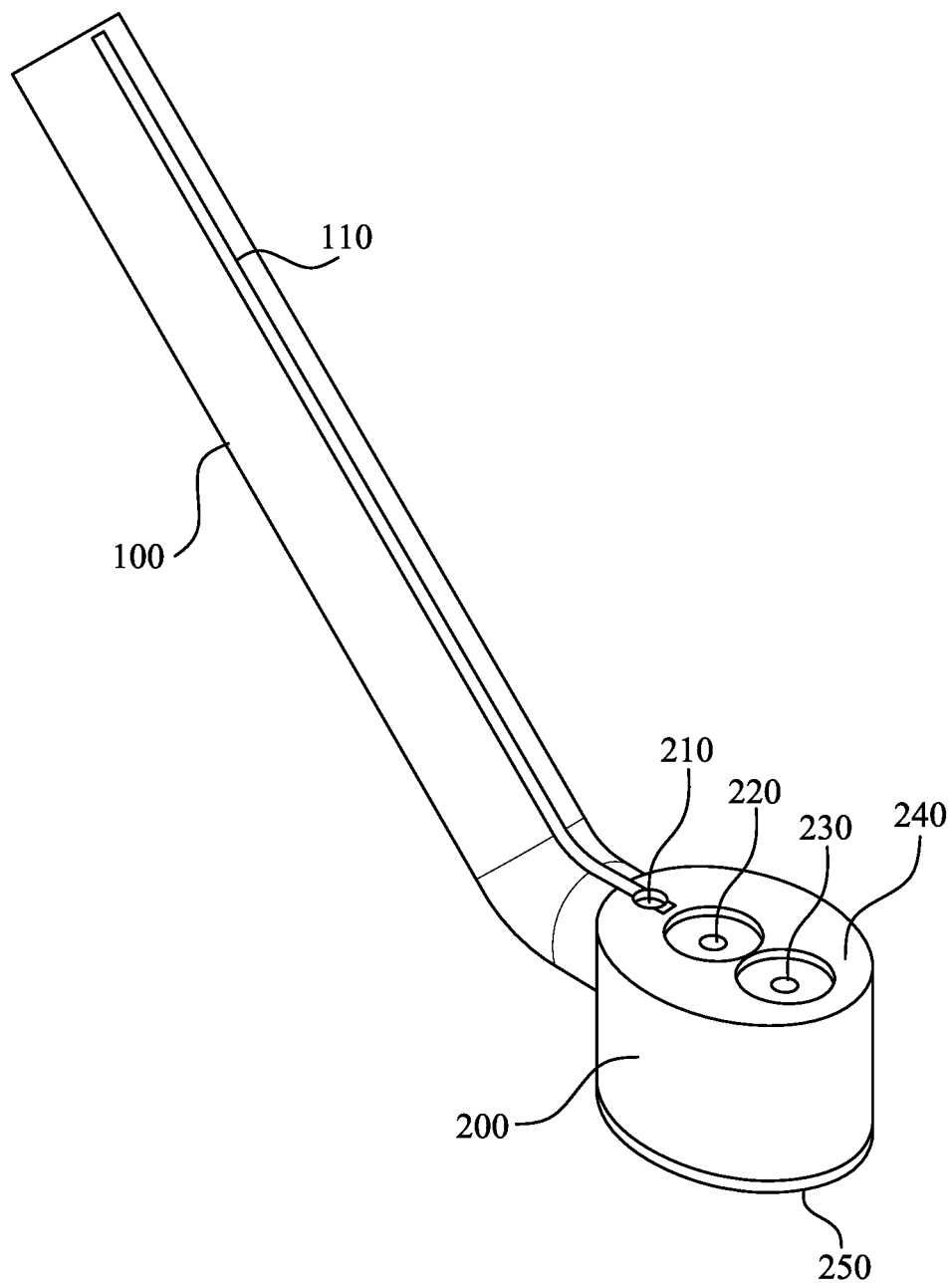
FIG. 3D. Design details of a 3 holed embodiment of the bullet sleeve (front-side view of right side of bullet sleeve) showing position of groove in relation to holes A, B and C. Handle (100), groove in handle (110), and functional unit (200) with holes A (210), B (220) and C (230). Inset around holes B and C provides space for radio-opaque metal guide which in this embodiment is circular. Anterior loading surface (240) and posterior/skin surface (250).

The unit has an anterior and posterior surface designated as a loading surface (240) and as a skin surface (250) and as shown by FIG. 3D. Preferably, there is about a 5 mm, preferably about 4.5 mm, 4.0 mm, 3.5 mm or 3.0 mm, fixed distance between each hole as well as a divergent angle between holes A and B, and holes A and C ranging from 3 degrees to 20 degrees, preferably from 5 to 15, 8 to 12 or 9-11 degrees. The amount of divergence is predesigned into the device so as to provide a customized device for a specific fracture. Holes are predesigned to be tight fit for the introduced Kirschner wire. In this context the Kirschner wire is held snugly in the hole but may be advanced through the hole by the application of force/pressure, e.g., about 5 lbs force, about 10 lbs force, about 15 lbs force, about 20 lbs force, about 25 lbs force, and preferably no more force than is necessary for a surgeon to comfortably advance the wire through the hole without bending the wire or otherwise displacing the position of the bullet sleeve. Typical holes sizes of 1.7, 1.9 and 2.1 mm are used for K-wire having diameters of 1.6, 1.8 and 2 mm. In other embodiments, the hole size is somewhat larger than the surgical wire that will be laterally inserted through it, for example, the hole can be >0, 0.01, 0.02, 0.03, 0.04, 0.05, 0.06, 0.07, 0.08, 0.09, 0.1, 0.11, 0.12, 0.13, 0.14, or 0.15 mm larger than the corresponding wire. The minute tight fit space allows for precise control of the wire and its trajectory.

Figure 4A:
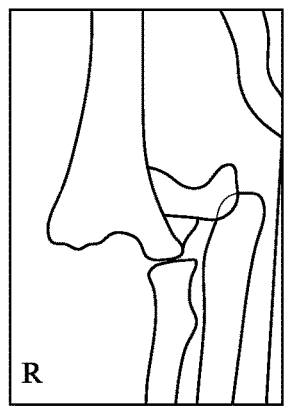
FIGS. 4A-4F shows a case example of a method of using the bullet sleeve device of the invention similar to that shown by FIGS. 3A-3D.
Figure 4B:
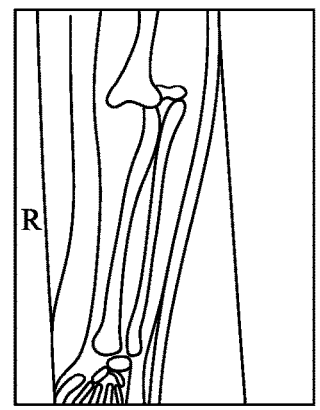
Figure 4C:
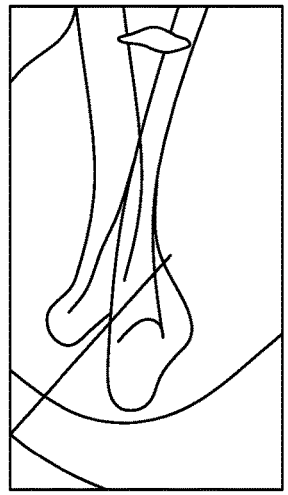
Figure 4D:
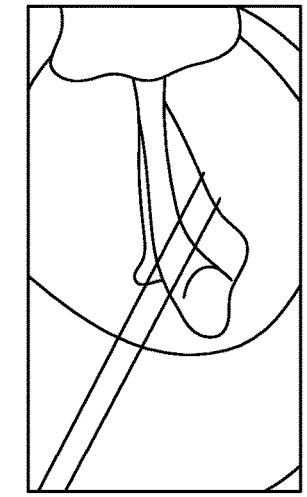
Figure 4E:
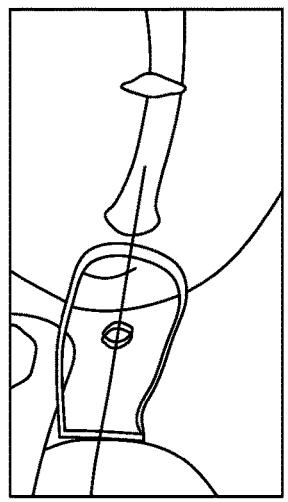
Figure 4F:
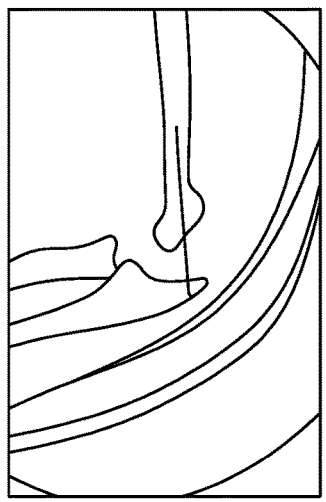
Figure 6A:
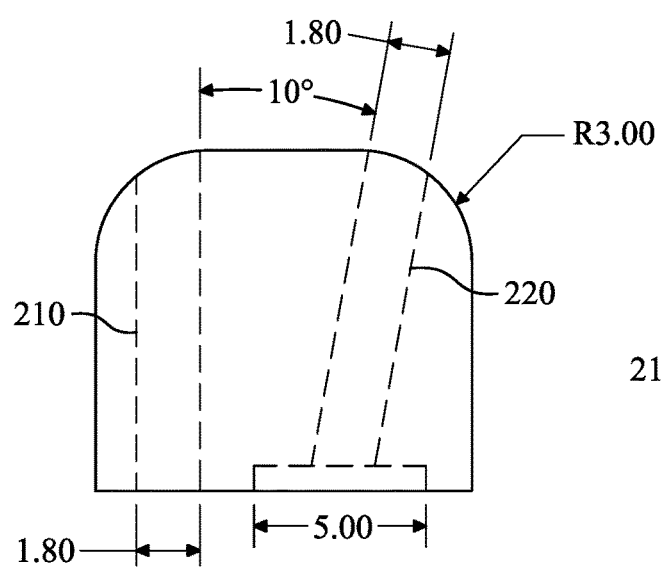
FIGS. 6A-6D show design detail of a 2 holed bullet sleeve as disclosed herein. The devices as shown by FIGS. 5A-5F and FIGS. 6A-6D all provide the surgeon with the option of fixing the fracture with 2 or 3 wires.
Figure 6B:
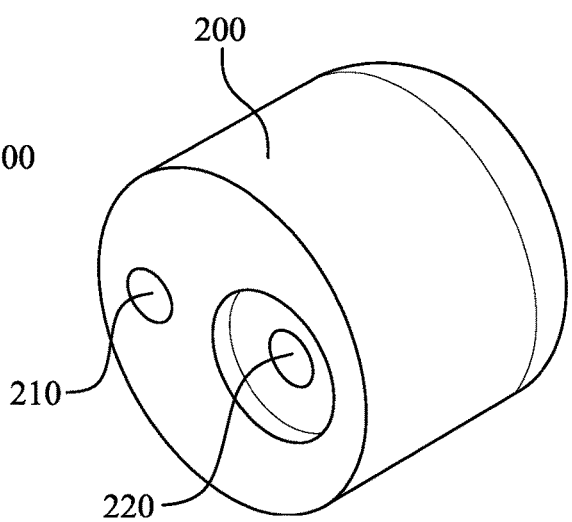
Figure 6C:
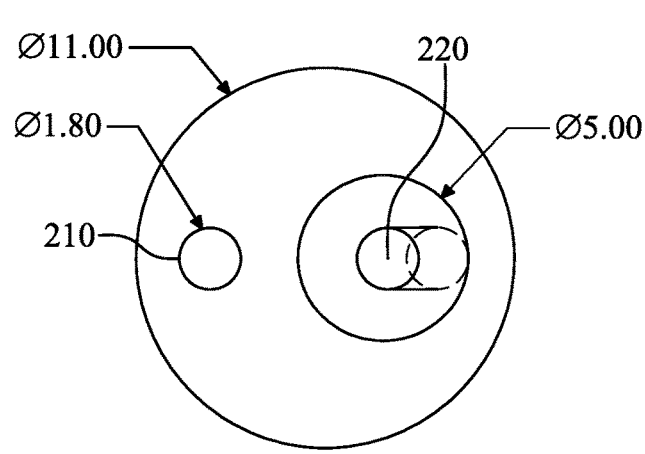
Figure 6D:
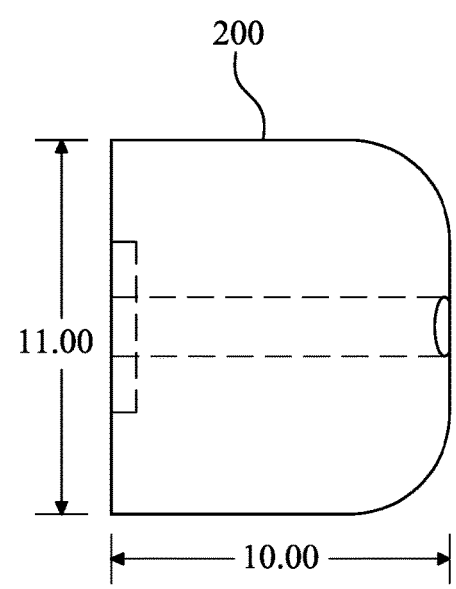

Holes B and C, if C is present, preferably have an x-ray opaque, metal circular or flat washer or donut-shaped guide which can be placed in a depressed inset around the hole which will assist in direction under radiographic imaging; see FIG. 2, FIG. 4E, and FIG. 6B.

The skin surface of the supracondylar fracture bullet sleeve device is smooth and curved to allow for good compressive contact with no focused or concentrated pressure points on the patient's skin. The functional unit is typically attached to the holding limb at an angle of 20-120, 20-80, 30-60, or 40-50 degrees, preferably at an angle of about 45 degrees, and is used to steer the functional unit as seen fit by the operator.

The first, most medial, wire inserted laterally with a free hand is typically used as a starting point as the bullet sleeve will slide over it using hole A. This can be accomplished by rotating the device around that wire in hole A.

Rotation is optimized and assessed with imaging using the radio-opaque metal washer over hole B and C (when C is present) as guide for alignment. Moreover, the holding limb has a groove extending throughout and reaching hole A in the functional unit that allows for an assisted visual estimation of alignment.

A simple introduction of K-wire through the loading surface into hole B and C (when C is present) after obtaining desired alignment, results in two (or 3) k-wires at a distance and angle of divergence as per evidence based recommendations. When the device has holes A and B, two wires can be inserted via these holes; when the device has holes A, B and C, three wires can be inserted using each hole.

Using the bullet sleeve decreases fixation time significantly, decreases radiation exposure to the patient and the operating team, and yields reliable textbook recommended supracondylar fracture fixation that would other otherwise require a surgeon having years of trial-and-error experience. Unlike other sleeves or guides the supracondylar bullet sleeve of the invention provides and uses the angular divergence that is recommended for fixation of a particular fracture and the device is sized for convenient use of the skin surface of a patient.

This design provides a smooth skin surface functioning unit with multiple wire/guide wire/drill bit introducing holes with predesigned angular discrepancies to facilitate percutaneous fixation of a fracture; a spacing between holes starting at about 5 mm, and a preselected divergence or convergence in the angles of holes A and B or holes A and C.

As shown by FIG. 2 and FIG. 3D, the device comprises a handle (100) and a functional unit (200) which holds and guides the fixation wires in the desired parameters in an objective manner. As shown by FIG. 2, the oval, elliptical or round functional unit (200) has three holds, hole A (201), hole B (220) and hole C (230). As shown by FIG. 3B, the functional unit (200) has an anterior (240) and posterior (250) surface designated as loading surface and skin surface.

The skin surface is smooth and curved to allow for good compressive contact with no pressure points. As shown by FIG. 6B, the skin surface side of the functional unit may be smoothed or rounded. Holes A and B and holes A and C are placed at relative angles to one another of about 3 to 20 degrees. As shown by FIG. 5C, holes B and C may be inclined relative to hole A at the same angle and be distanced from each other by about 5 mm (4.48 mm). In another embodiment, there is about a 5 mm fixed difference between holes A and B and B and C as measured on the loading surface of the functional unit.

Holes B and C typically have one or more metal circular guides which assist in directing the wire under radiographic imaging. As shown by FIGS. 2 and 3D, holes B and C on the anterior loading surface may be surrounded by a depressed inset in the functional unit which can accommodate a radio-opaque washer-like element or other radiopaque marker. The inset may be any shape, such a regular or irregular polygon, but is typically circular. The washer-like element or other radio-opaque marker is generally inserted or applied after production of the functional unit, for example, after the functional unit is 3D printed. The washer-like element also has a hole and is placed so as to not block insertion of surgical wire into hole B or hole C. In other embodiments, the radio-opaque marker may be printed on the surface of the device.

As shown by FIGS. 2 and 3D, the functional unit (200) is typically attached at an angle of about 45 degrees to the holding limb (100) which is used to steer the functional unit as seen fit by the operator. The holding limb has a groove (110) extending throughout and reaching hole A (210) in the functional unit (200). This groove allows for an assisted visual estimation of alignment.

The supracondylar bullet sleeve device disclosed herein incorporates several unique features distinguishing it from other medical devices including simplicity and ease of use which facilitates placing multiple K-wires or other surgical wires or pins in closed surgical reduction procedures. The device as disclosed herein is used in a manner that does not damage underlying skin or tissue and does not require opening of the skin characteristic of open surgical reductions. It does not require special serrated or tethered edges used in devices used for open reductions and the device itself does not need to penetrate the skin such as cylindrical devices used in some open reductions.

The device as disclosed herein does not require bending of introduced surgical wires after placement which could hinder usage of a power drill during surgical wire insertion. The device of the invention does not alter the trajectory of the surgical wire going into the functional unit thus providing for a more accurate insertion during a closed surgical reduction. In contrast to surgical devices which alter the trajectory of a surgical wire, the device as disclosed herein has a predesigned fix angle throughout the device which guides the inserted wire on a fixed trajectory.

Unlike devices with parallel holes, the bullet sleeve of the present disclosure has parallel holes with different trajectories and angulation. The device as disclosed herein is simple and does not require a coupling system or attachable or detachable device elements. The device as disclosed herein can rely on loading of a k-wire onto the hole B while using the previously inserted wire in hole A as a reference to reach a direction and a position at the recommended angle. The internal angulation in the device disclosed herein employs simple divergence between the first introduced wire and a second fixed wire to obtain an excellent resilient fixation and not based on anatomic resemblances or shapes.

Overall, the device of the present disclosure may have one or more components made of radiolucent material thus the inclusion of the radio-opaque material in the form of washer-like elements permit adequate assessment of the position of the device under imaging, e.g., x-rays. The device and method of the present disclosure do not require internal fixation using intramedullary nails.

Surgical reduction of a fracture. Reduction is a surgical procedure to repair a fracture or dislocation to the correct alignment. This sense of the term "reduction" does not imply any sort of removal or quantitative decrease but rather implies a restoration. When a bone fractures, the fragments lose their alignment in the form of displacement or angulation. For the fractured bone to heal without any deformity, the bony fragments must be re-aligned to their normal anatomical position. Orthopedic surgery attempts to recreate the normal anatomy of the fractured bone by reduction of the displacement. Reduction may be performed using "closed" or "open" methods. Open reduction is where the fracture fragments are exposed surgically by dissecting the tissues. Closed reduction is the manipulation of the bone fragments without surgical exposure of the fragments. Typically before fixation of bones or bone fragments produced by a supracondylar fracture, a closed reduction is performed, then the bones or bone fragments are fixed using the supracondylar bullet sleeve device as disclosed herein.

Kirschner wire or K-wires are sterilized, sharpened, smooth stainless steel pins. They come in different sizes and are used to hold bone fragments together (pin fixation) or to provide an anchor for skeletal traction. Kirschner wires come in a variety of sizes. As they increase in size they become less flexible. Some representative sizes range from <0.7, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 and >2.5. The diameter of holes A, B and/or C of the invention may be selected to provide a tight fit for a Kirschner wire or other surgical wire or pin. Other kinds of surgical, orthopedic or medical guidewires, reinforcement or pins may be used. In some embodiments, the surgical wire is threaded to help prevent movement or backing out once placed, in other embodiments it is not threaded which often provides a stronger wire.

Kirschner wires or pins are often driven into the bone through the skin (percutaneous pin fixation) using a power or hand drill. In some surgical procedures they can form part of an Ilizarov apparatus. After definitive fixation, the Kirschner wires can be removed.

Gartland classifications of supracondylar fractures include types I, II, IIA, IIB, III, IIIA, IIIB and IV. *Vineet, Kumar; Ajai, Singh* (1 Dec. 2016). "Fracture Supracondylar Humerus: A Review". Journal of Clinical and Diagnostic Research. 10 (12): 1-6. doi:10.7860/JCDR/2016/21647.8942. PMC 5296534. PMID 28208961 (incorporated by reference).

Production of surgical device. The surgical device disclosed herein may be constructed by methods known in the art of any durable or strong material. It may comprise plastics (preferably a fluorinated polymer such as PTFE or Teflon), ceramics, glass, 3D printing resins or inks, or other suitable materials.

3D Printing. MRI and computed tomography (CT) may be used to construct a 3D image of a supracondylar fracture, especially a reduced supracondylar fracture.

A model of the fracture is produced and used to design an external surgical guide. The external surgical guide may be 3D printed by methods known in the art.

Any type of 3D printer can be used to print a model of a reduced supracondylar fracture and corresponding surgical device as disclosed herein. 3D printer manufacturers include those listed at Hypertext transfer protocol secure://_en.wikipedia.org/wiki/List_of_3D_printer_manufacturers (last accessed May 17, 2019, incorporated by reference). Use of 3D printing for orthopedic purposes is described by Hypertext transfer protocol secure://_medimodel.com/article/3d- printing-orthopaedic-surgery/ (accessed online May 17, 2019); incorporated by reference) and to Hypertext transfer protocol secure://_medimodel.com/article/3d-printing-in-orthognathic-surgery (accessed online May 17, 2019)/. Any suitable 3D printer or 3D ink/resin may be used to make the surgical guide of the invention. In one embodiment VisiJet® M2 Sup as described in the Safety Data Sheet Revision Date: Jul. 11, 2017 may be used in conjunction with a ProJet® 2500 system (Hypertext transfer protocol secure://_www.3dsystems.com/3d-printers/projet-mjp-2500-series), both last accessed May 17, 2019, and both incorporated by reference. Additional information about 3D printing is also available at VisiJet® M2 Sup: Hypertext transfer protocol://infocenter.3dsystems.com/materials/sites/default/files/sds-files/professional/VisiJet_M2/24224-512-02-A%2CSDS%20GHS%2CEnglish%2CVisiJet%20M2%20Sup.pdf (revision date Apr. 11, 2018, incorporated by reference).

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of Hypertext transfer protocol: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

The ranges disclosed herein include all intermediate values and subranges as well as the endpoints of the ranges unless otherwise specified.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for treating a supracondylar fracture comprising:
reducing the fracture,
steering a surgical device to a location on the skin of a subject proximal to the reduced fracture,
introducing a K-wire or other surgical wire into a hole A and a hole B and, optionally, into a hole C, through the skin, and into one or more bones or bone fragments of the subject,
wherein the surgical device comprises:
a handle suitable for a surgeon to steer the surgical device on skin and having a longitudinal groove suitable for visual alignment of surgical wires introduced into the device, and
a functional unit comprising the holes A and B, and optionally C, which is suitable to hold and guide surgical wires;
wherein the handle is about 50 to 100 mm long and has an average diameter of about 6-10 mm and wherein the handle is connected at its lower end to one side of the functional unit at an angle ranging from about 30-60 degrees;
wherein the functional unit has an anterior and a posterior side and has an average cross-sectional diameter ranging from about 15-30 mm, a vertical thickness between said anterior and posterior sides ranging from about 10-20 mm;
wherein the functional unit comprises the holes A and B and optionally C, which penetrate the anterior and posterior sides of the functional unit;
wherein each of the holes A and B, or A, B and C is about 1.6 to 2.5 mm in diameter;
wherein the holes A and B, and holes B and C, when C is present, are about 4-6 mm fixed distance from one another; and
wherein a top of each of the holes A and B, and optionally C, is linearly aligned with each other along the anterior surface of the functional unit and with the longitudinal groove of the handle.

2. The method of claim 1, wherein the handle of the surgical device has a substantially circular or oval cross-section, the functional unit has a substantially circular, elliptical, or oval cross-section, and the functional unit holes A and B, or holes A, B and C, have substantially round or oval cross-sections.

3. The method of claim 1, wherein the handle of the surgical device has a substantially circular, elliptical, or oval cross-section and is about 54-74 mm long and wherein the handle is connected at its lower end to the functional unit at an angle ranging from about 40-50 degrees,
wherein the functional unit has a substantially circular, elliptical, or oval cross section and has an average diameter of about 20-24 mm and a vertical thickness ranging from about 13-17 mm,
wherein the functional unit holes A and B, or holes A, B and C, said holes having substantially round, elliptical, or oval cross sections about 1.8-2.0 mm in diameter,
wherein the vertical alignment of holes A and B or holes A and C as measured by the alignment of the holes through the body of the functional unit diverge by about 3-20 degrees.

4. The method of claim 1, wherein the handle of the surgical device has a substantially circular, elliptical, or oval cross-section and is about 64 mm long and wherein the handle is connected at its lower end to the functional unit at an angle ranging from about 45 degrees,
wherein the functional unit has a substantially circular, elliptical, or oval cross section and has an average diameter of about 22 mm and a vertical thickness ranging from about 15 mm,
wherein the functional unit holes A and B, or holes A, B and C, have substantially round, elliptical, or oval cross sections about 1.7, 1.9 or 2.1 mm in diameter,
wherein the vertical alignment of holes A and B or Holes A and C diverge by about 3-20 degrees, and wherein holes A and B, or holes A, B and C are about 5 mm fixed distance from one another.

5. The method of claim 1, wherein both holes B and C are present and the vertical alignment of holes A and B and holes A and C diverge at the same angle between 3 and 20 degrees.

6. The method of claim 1, wherein both holes B and C are present and the vertical alignment of holes A and B and holes A and C diverge at different angles.

7. The method of claim 1, wherein the subject has a Type IIA or Type IIB supracondylar fracture.

8. The method of claim 1, wherein the subject has a Type IIIA or Type IIIB supracondylar fracture.

9. The method of claim 1, wherein said subject has a Type IV supracondylar fracture.

10. The method of claim 1, wherein the subject is less than 5 years old.

11. The method of claim 1, wherein the subject is at least 5 years old and no more than 9 years old.

12. The method of claim 1, wherein the subject is more than 9 years old.

13. The method of claim 1, wherein the subject has or is at risk of vascular insufficiency due to the supracondylar fracture.

14. The method of claim 1, wherein the subject has or is at risk of neurological deficit due to the supracondylar fracture.

15. The method of claim 1, wherein the subject has or is at risk of forearm compartment syndrome associated with the supracondylar fracture.

16. The method of claim 1, wherein the subject has or is at risk of malunion associated with the supracondylar fracture.

\* \* \* \* \*